United States Patent [19]

Wei et al.

[11] 4,275,065

[45] Jun. 23, 1981

[54] MODULATING THE IMMUNE RESPONSE WITH 2-SUBSTITUTED-3-HYDROXY-THIAZOLO[2,3-b]BENZO(AND AZABENZO)THIAZOLIUM SALTS AND MESOIONIC DIDEHYDRO DERIVATIVES THEREOF

[75] Inventors: Peter H. L. Wei, Springfield; Francis J. Gregory, Berwyn, both of Pa.

[73] Assignee: American Home Products Corporation, New York, N.Y.

[21] Appl. No.: 130,483

[22] Filed: Mar. 31, 1980

Related U.S. Application Data

[63] Continuation-in-part of Ser. No. 50,847, Jun. 21, 1979, abandoned.

[51] Int. Cl.³ .................. A61K 31/44; A61K 31/425; C07D 513/04; C07D 513/14
[52] U.S. Cl. .................................... 424/256; 424/270; 546/83; 546/114; 548/151; 548/165; 548/169; 548/173; 548/174
[58] Field of Search ..................... 546/83; 548/151; 424/270, 256

[56] References Cited

U.S. PATENT DOCUMENTS

| 2,424,483 | 7/1947 | Middleton et al. ............. 548/151 X |
| 2,790,172 | 4/1957 | Rudner ............................ 548/151 X |
| 3,714,170 | 1/1973 | Dohmori et al. ..................... 546/83 |

FOREIGN PATENT DOCUMENTS

41-17215  9/1966  Japan .

OTHER PUBLICATIONS

Potts, K., et al., *J. Org. Chem.,* 43(13), 1978, pp. 2697–2700.
Ollis, W., et al., in *Advances in Heterocylic Chemistry* (Katritzky, et al., Editors), vol. 19, Academic Press, New York, 1976, pp. 1–5.
Cagnoli, N., et al. *Gazz. Chim. Ital.,* 95(6), 1965, pp. 615–623.

*Primary Examiner*—Richard A. Schwartz
*Attorney, Agent, or Firm*—George Tarnowski

[57] ABSTRACT

Novel 2-substituted-3-hydroxythiazolo[2,3-b]benzo- (and azabenzo)thiazolium salts, the mesoionic didehydro derivatives thereof and related compounds are disclosed, as well as the use thereof as modulators of the immune response.

18 Claims, No Drawings

MODULATING THE IMMUNE RESPONSE WITH 2-SUBSTITUTED-3-HYDROXYTHIAZOLO[2,3-b]BENZO(AND AZABENZO)THIAZOLIUM SALTS AND MESOIONIC DIDEHYDRO DERIVATIVES THEREOF

This is a continuation-in-part of U.S. Ser. No. 50,847 filed June 21, 1979 now abandoned.

BACKGROUND OF THE INVENTION

The invention relates to novel 2-substituted 3-hydroxythiazolo[2,3-b]benzothiazolium salts, 2-substituted thiazolo-[2,3-b]benzothiazol-3(2H)-one mesoionic didehydro derivatives, 2-substituted thiazolo[2′,3′-2,3]-thiazolo[5,4-b]pyridin-3(2H)-one mesoionic didehydro derivatives and related compounds, and their use as modulators of the immune response.

In recent years, the rapid upsurge in immunological research has brought about a greater appreciation and understanding of the complexities of the immune response. While the traditional overall view of the immune system remains, new discoveries have radically changed some thinking about the details of the system. Thus, the immune system is still divided into humoral immunity, populated with B cells and responsible for antibody formation, and cell-mediated immunity, populated with T cells and responsible for the rejection or organ transplants or skin grafts, as well as the defense mechanism against various foreign biological matter and endogenous neoplastic growths.

It is only in the last decade or so, however, that the concept has been accepted that different cell populations interact in the induction and expression of both humoral and cell-mediated immunity. Thus, subpopulations of B cells and T cells have been described, such as for example "suppressor" and "helper" T cells. In a number of animal models, it has been postulated that the helper T cells act in the induction of a complete antibody response to many antigens, whereas T suppressor cells are capable of preventing or terminating such responses. It is now believed that positive and negative cellular interactions control the ultimate degree of immune response. So, it is believed that any given immune response is regulated, and that the degree and mode of regulation may ultimately explain the various reactions, diseases, and disorders which are the manifestations of the operation of the organism's immune system.

The T cell subpopulations of suppressor and helper T cells have been implicated in a number of immune response manifestations. Thus, the loss of suppressor T cells is now believed to be a major factor in such autoimmune connective tissue disease as systemic lupus erythematosus. Moreover, in the latter case, as well as in probable impaired immune system responses such as rheumatoid arthritis, it is believed that the helper T cells exacerbate the condition.

Also, the theory has been advanced that T suppressor cell hypofunctioning, resulting in inadequate T-B cell cooperation in the immune response, with continuous B cell stimulation and subsequent antibody production may be the cause of the production of antigen-antibody complexes which are the causative agents of renal and inflammatory processes in arthritis and autoimmune diseases.

Thus, it is now apparent that a number of lymphopoietic disorders are undoubtedly associated with abnormalities of T cell and especially suppressor cell function. The loss of suppressor function is at least an early event in certain immune response diseases and is a disease-perpetuating mechanism in others. The loss of suppressor function probably leads to excessive lymphoid cell proliferation and may significantly contribute to lymphoproliferative disorders. The conditions created thereby may be exacerbated by helper T cells.

The role of immunomodulatory agents in the treatment of immune diseases and disorders, as well as in the attempt to prolong the life of organ transplants and skin grafts, has been to suppress the immune response, especially of cell-mediated immunity. By suppressing the cell-mediated immune response, it is possible to delay and possibly prevent the host organism from rejecting a skin graft or organ transplant, or the graft from immunologically rejecting the host (graft vs. host reaction). Similarly, enhancing or reinstituting suppressor function by immunomodulator therapy is a beneficial course of treatment for antoimmune and probable antoimmune diseases and disorders. However, the current immunosuppressive agents have the serious drawback that in effective doses they suppress the entire immune response. Thus, they suppress both the cell-mediated and humoral immunity, with the result that the patient is left without immunity to infections which he could otherwise readily overcome without medical aid. Thus, the hitherto known immunosuppressive agents are not selective in their action.

The compounds of the present invention, however, are highly selective immunomodulatory agents which are especially indicated in the treatment of various skin graft and organ transplant reactions, and immune system diseases and disorders such as systemic lupus erythematosus and rheumatoid arthritis, whose etiology is probably suppressor T cell dysfunction.

DETAILED DESCRIPTION OF THE INVENTION

The invention is directed to novel compounds having the general formula:

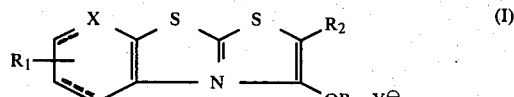

or

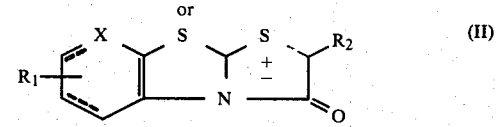

wherein $R_1$ is hydrogen, halo, amino, lower alkyl, lower alkoxy, trifluoromethyl or hydroxy; $R_2$ is lower alkyl, acetyl, trifluoroacetyl, phenyl or phenyl substituted with fluorine, chlorine, bromine, lower alkyl, lower alkoxy, amino, nitro and trifluoromethyl; $R_3$ is hydrogen or lower alkanoyl; X is CH or N, with the proviso that when $R_1$ is hydrogen and X is CH, $R_2$ is a substituent other than lower alkyl; and Y is $CF_3CO_2^{\ominus}$, or a halide, and where the dotted lines represent optional double bonds in the 5,6 and 7,8 positions.

The invention is further directed to a method of modulating the immune response in warm-blooded animals in need of modulation of the immune response by administering to a warm-blooded animal an amount effective to bring about said modulation of the immune response of a compound having the general formula:

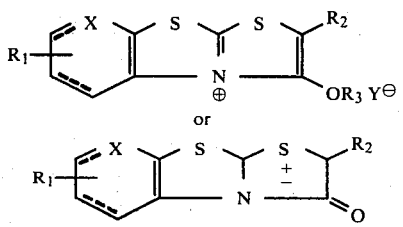

wherein $R_1$ is hydrogen, halo, amino, lower alkyl, lower alkoxy, trifluoromethyl or hydroxy; $R_2$ is lower alkyl, acetyl, trifluoroacetyl, phenyl or phenyl substituted with fluorine, chlorine, bromine, lower alkyl, lower alkoxy, amino, nitro and trifluoromethyl; $R_3$ is hydrogen or lower alkanoyl; X is CH or N; and Y is $CF_3CO_2^{\ominus}$ or a halide, and where the dotted lines represent optional double bonds in the 5,6 and 7,8 positions.

The term "lower alkyl" when used herein includes straight and branched chain hydrocarbon radicals having from 1 to about 6 carbon atoms. The terms "lower alkoxy" and "lower alkanoyl" in like manner designate radicals in which the hydrocarbon portion has 1 to about 6 carbon atoms.

The terms "halo" and "halide" when used herein refer to radicals of the elements fluorine, chlorine and bromine and chlorine and bromine, respectively.

The compounds of the invention having the general formula:

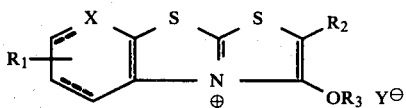

wherein $R_1$, $R_2$, $R_3$ and Y are defined as hereinbefore, X is CH, and the dotted lines represent optional double bonds in the 5,6 and 7,8 positions, can be readily prepared by a cyclization reaction in which a suitably substituted 2-mercaptobenzothiazole (or where X is N, a suitably substituted 2-mercapto-tetrahydro- or 2-mercaptothiazolo[5,4-b]pyridine) is condensed with a suitably substituted α-halo acetic acid in the presence of a condensing agent:

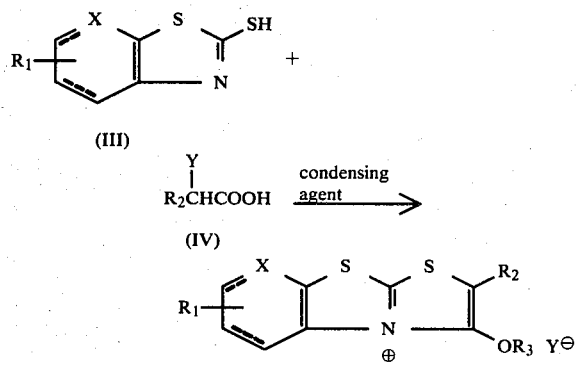

In this reaction sequence, the final product may exist in the form of the 3-hydroxy compound, or in the form of which $R_3$ is the residue of the condensing agent. The reactants, in an organic solvent, such as for example acetone, and the condensing agents, such as for example a mixture of acetic acid and acetic anhydride, trifluoroacetic anhydride and the like are heated until the solvent volume is reduced and a precipitate deposited. The precipitated solid is recrystallized to yield the desired 2-substituted-3-hydroxythiazolo[2,3-b]benzothiazolium salts and 2-substituted-3-hydroxythiazolo[2,3-b]azebenzothiazolium salts. In a variant of this preparation, a two step process can be employed in which a suitably substituted 2-benzothiazolylthioglycolic acid is prepared in the first step, followed by cyclization in the presence of a condensing agent in the second step:

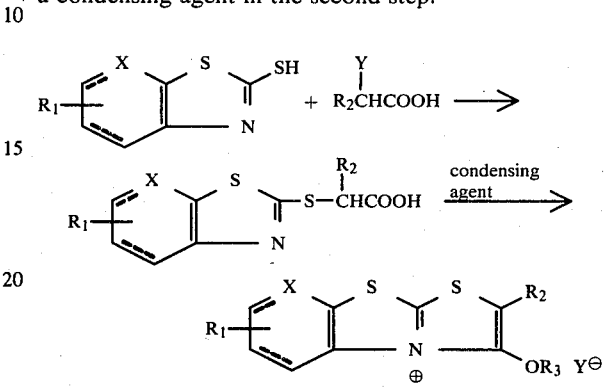

Again, in the final product $R_3$ may be hydrogen or the residue of the condensing agent. In the case of either preparation sequence in which $R_3$ is the condensing agent residue and where it is desired to obtain the compound in which $R_3$=H, the condensing agent residue can be readily removed by conventional means, as for example deacylation by heating in certain solvents. Also, in those instances in which $R_1$ is amino or hydroxy, the latter groups can be protected from acylation during the cyclization reaction by use of conventional protecting groups, for example tosyl, benzyloxycarbonyl, tert-butyloxycarbonyl and the like for the amino group, and acetyl, benzoyl, tert-butyl, benzyl and the like for the hydroxy group. The protecting groups can be readily removed by conventional techniques after cyclization is complete.

These benzothiazolium salts can also be transformed into their mesoionic didehydro derivatives:

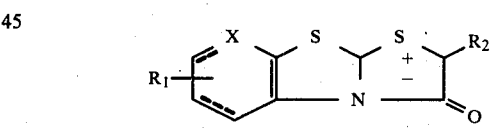

The transformation can be carried out by dissolving the benzothiazolium or azabenzothiazolium salts in a methylene chloride/water mixture, separating the organic and aqueous layers and concentrating the organic (methylene chloride) layer to recover the mesoionic didehydro derivative, which can then be further purified by recrystallization.

The compounds of the invention are immunomodulators of high selectivity, having particular activity on the cell-mediated immune system without impeding the humoral immune mechanisms. The compounds have therapeutic application in a variety of situations in which immunomodulation is indicated. Thus, the compounds are useful in treating allograft reactions, organ transplant reactions, and graft vs. host reactions. The compounds permit the host to accept the graft without destroying the host's immunity to other infections. The compounds are also useful in the treatment of autoimmune diseases, such as systemic lupus erythematosus (SLE). Further, the compounds of the invention inhibit the production of the immunoglobulins, which are so pathologic to autoimmune disease such as SLE, as well as the production of antigen-antibody complexes which are the causative agents of renal and inflammatory processes in arthritis and autoimmune diseases. Thus, the compounds of the invention are also useful in the treatment of such conditions as rheumatoid arthritis.

When the compounds of the invention are employed as immunomodulators, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth methyl cellulose, sodium carboxymethyl cellulose, low melting wax, cocoa butter, and the like. Diluents, flavoring agents, solubilizers, lubricants, suspending agents, binders, tablet-disintegrating agents and the like may be employed. The compounds may be encapsulated with or without other carriers. In all cases the proportion of active ingredients in said compositions both solid and liquid will be at least sufficient to impart immunomodulatory activity thereto on oral administration. The compounds may also be injected parenterally, in which case they are used in the form of a sterile solution containing other solutes, for example, enough saline or glucose to make the solution isotonic.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached. In general, the compounds of the invention are most desirably administered at a concentration level that will generally afford effective results without causing any harmful or deleterious side effects. With large animals (about 70 kg. body weight), for injection administration the dose is from about 25 milligrams to about 50 milligrams and for oral administration the dose is from about 50 milligrams to about 200 milligrams and preferably from about 50 milligrams to about 100 milligrams per day either as a single unit dose, or if desired, the dosage may be divided into convenient subunits administered at convenient times throughout the day.

The immunomodulatory effect of the compounds of the invention may be demonstrated by standard pharmacological and histological procedures. The pharmacological procedures are described more fully in the examples given hereinafter.

These procedures illustrate the ability of the compounds of the invention to exert an immunomodulatory effect, especially selectively on the cell-mediated immunity by directly measuring the effect of the compounds on the humoral and cell-mediated immunity, by their effect on thymus-lymphocyte production, by hemolytic plaque technique (Jerne test), response to autoimmune disease (SLE and hemolytic anemia) in NZB/W $F_1$ mouse and NZB rodent, by the guinea pig delayed (tuberculin) hypersensitivity test and the adjuvent arthritis test.

EXAMPLE 1

6-Chloro-3-hydroxy-2-phenylthiazolo-[2,3-b]benzothiazolium bromide

A 1 l. acetone solution of 10.25 g. (0.05 moles) 5-chloro-2-mercaptobenzothiazole and 10.75 g. (0.05 moles) α-bromophenylacetic acid containing 100 ml. glacial acetic acid and 30 ml. acetic anhydride is heated in an open flask until the volume reaches 300 ml. The precipitated solid, weighing 16 g. (80% yield) is collected and recrystallized from glacial acetic acid. The product melts at 225°–228° C.

Analysis for: $C_{15}H_9ClNOS_2Br$. Calculated: C, 45.18; H, 2.28; N, 3.51; Cl, 8.89; S, 16.08. Found: C, 45.15; H, 2.36; N, 3.47; Cl, 8.70; S, 16.19.

EXAMPLE 2

3-Hydroxy-2-phenylthiazolo-[2,3-b]benzothiazolium bromide

A 1 l. acetone solution of 33.4 g. (0.20 moles) 2-mercaptobenzothiazole and 43 g. (0.20 moles) α-bromophenylacetic acid containing 75 ml. glacial acetic acid and 50 ml. acetic anhydride is heated in an open flask to a volume of 400 ml. The precipitated yellow solid is collected and washed with acetone or ether and dried. The product, weighing 47.7 g. (65% yield) melts at 215° C. (dec.).

Analysis for: $C_{15}H_{10}NOS_2Br$. Calculated: C, 49.45; H, 2.77; N, 3.85; Br, 21.94; S, 17.60. Found: C, 49.27; H, 2.75; N, 3.78; Br, 21.98; S, 18.00.

EXAMPLE 3

6-Chloro-2-phenylthiazolo[2,3-b]benzothiazol-3(2$\underline{H}$)-one mesoionic didehydro derivative 26 g. of 6-chloro-3-hydroxy-2-phenylthiazolo[2,3b-]benzothiazolium bromide prepared according to Example 1, is suspended in a mixture of 3 l. methylene chloride and 1 l. water. The mixture is stirred at room temperature until all the solid is dissolved. The layers are separated and the methylene chloride layer is dried over anhydrous magnesium sulfate. The drying agent is removed by filtration and the filtrate is concentrated to dryness. The residual solid is triturated with acetone and the solid is collected. The crude material is recrystallized from 350 ml. of methylene chloride. The purified material weighs 14.3 g. (69% yeidl) and melts at 206°–208° C.(dec.).

Analysis for: $C_{15}H_{18}ClNOS_2$. Calculated: C, 56.88; H, 2.54; N, 4.41; Cl, 11.16. Found: C, 56.40; H, 2.46; N, 4.42; Cl, 11.22.

EXAMPLE 4

2-Phenylthiazolo[2',3'-2,3]thiazolo[5,4-b]-pyridin-3(2$\underline{H}$)-one mesoionic didehydro derivative A. α-(Thiazolo[5,4-b]-pyridin-2yl-thio)phenyl acetic acid 6.5 g. (0.03 moles) α-bromophenylacetic acid and 6.2 g. (0.03 moles) potassium salt of 2-mercaptothiazolo[5,4-b]pyridine are suspended in 200 ml. acetone and the mixture is stirred at room temperature overnight. The mixture is filtered and the filtrate concentrated to dryness. The resulting compound is an oil and is not isolated.

B. 3-Hydroxy-2-phenylthiazolo[2',3'-2,3]thiazolo-[5,4-b]pyridinium trifluoroacetate The compound of A above is dissolved in ether and 20 ml. of trifluoroacetic anhydride is added to the solution. The solid which forms immediately is collected, washed with ether and dried. The product weighs 9.7 g.

C. 2-Phenylthiazolo[2',3'-2,3]thiazolo[5,4-b]pyridin-3(2H)-one mesoionic didehydro derivative 8.5 g. of the compound of B above is suspended in a mixture of 200 ml. methylene chloride and 150ml. water and the mixture is stirred at room temperature for 30 minutes. The orange solid is collected and dried at 100° in vacuo. The compound weighing 5.0 g. (80% yield) melts at 216°–218° C.(dec.).

Analysis for: $C_{14}H_8N_2OS_2$. Calculated: C, 59.13; H, 2.83; N, 9.85; S, 22.55. Found: C, 59.06; H, 2.90; N, 9.79; S, 22.14.

EXAMPLE 5

6-Chloro-2-trifluoroacetylthiazolo[2,3-b]-benzothiazol-3(2H)-one mesoionic didehydro derivative 13.0 g. (0.05 moles) of (5-chlorobenzothiazol-2-yl-thio)acetic acid is dissolved in 300 ml. ether. 20 ml. of trifluoroacetic anhydride are added slowly. A maroon solid, which precipitates immediately, is collected and dried. The product, weighing 10.6 g. (63% yield) melts at 231°–233° C.(dec.).

Analysis for: $C_{11}H_3ClF_3NO_2S_2$. Calculated: C, 39.11; H, 0.89; N, 4.15; S, 18.99. Found: C, 39.17; H, 1.03; N, 4.12; S, 19.24.

EXAMPLE 6

6-Chloro-2-(p-chlorophenyl)thiazolo[2,3-b]-benzothiazol-3(2H)-one mesoionic didehydro derivative A. 6-Chloro-2-(p-chlorophenyl)thiazolo[2,3-b]benzothiazolium bromide An acetone solution of 10.0 g (0.05 moles) 5-chloro-2-mercaptobenzothiazole and 12.5 g. (0.01 moles) α-bromo-(p-chloro)phenylacetic acid containing 50 ml. glacial acetic acid and 20 ml. acetic anhydride is heated in an open flask. When the solution is concentrated to a small volume, the precipitated solid, weighing 15.1 g. (70% yield) is collected.

B. 6-Chloro-2-(p-chlorophenyl)thiazolo[2,3-b]benzothiazol-3(2H)-one mesoionic didehydro derivative 8 g. of the compound of A above is suspended in a mixture of methylene chloride and water, and the mixture is stirred at room temperature for 1 hour. The layers are separated, and the methylene chloride layer is dried over anhydrous magnesium sulfate. The drying agent is removed by filtration and the filtrate is concentrated to a small volume. The orange-red product, weighing 4.7 g. (67% yield) is collected and further recrystallized from methylene chloride. The analytical sample melts at 235°–237° C.

Analysis for: $C_{15}H_7Cl_2NOS_2$. Calculated: C, 51.14; H, 2.00; N, 3.98; Cl, 20.13; S, 18.21. Found: C, 50.75; H, 1.89; N, 4.00; Cl, 19.88; S, 17.91.

EXAMPLE 7

2-Phenylthiazolo[2,3-b]benzothiazol-3(2H)-one mesoionic didehydro derivative 37.7 g. (0.104 moles) of the compound prepared according to Example 2 are suspended in a 1:1 mixture of methylene chloride and water, and the mixture is stirred at room temperature for 30 minutes. The layers are separated and the methylene chloride layer is dried over anhydrous magnesium sulfate. The drying agent is removed by filtration and the filtrate is concentrated to a small volume. The precipitated orange solid is collected and recrystallized from methylene chloride. The product is recovered in 45% yield and melts at 172° C.(dec.).

Analysis for: $C_{15}H_9NOS_2$. Calculated: C, 63.58; H, 3.20; N, 4.94; S, 22.63. Found: C, 63.17; H, 3.30; N, 4.78; S, 22.81.

EXAMPLE 8

7-Ethoxy-3-hydroxy-2-phenylthiazolo[2,3-b]benzothiazolium bromide

A 2.5 l. acetone solution of 50.0 g. (0.237 moles) 6-ethoxyl-2-mercaptobenzothiazole and 51.0 g. (0.237 moles) α-bromophenylacetic acid containing 100 ml. glacial acetic acid and 100 ml. acetic anhydride is heated in an open flask until the solution is reduced to 2 l. The solution is allowed to stand at room temperature overnight. The precipitated solid is collected, washed with acetone and ether, and dried in an oven. The product, weighing 34.7 g. (36% yield), does not melt below 270° C.

Analysis for: $C_{17}H_{14}NO_2S_2 \cdot Br$. Calculated: C, 50.02; H, 3.46; N, 3.43; S, 15.70. Found: C, 50.04; H, 3.47, N, 3.71; S, 16.13.

EXAMPLE 9

7-Ethoxy-2-phenylthiazolo[2,3-b]benzothiazol-3(2H)-one mesoionic didehydro derivative 15 g. of 7-ethoxy-3-hydroxy-2-phenylthiazolo[2,3-b]benzothiazolium bromide, as prepared according to Example 8, is suspended in a mixture of 1000 ml. methylene chloride and 500 ml. water, and the mixture is stirred at room temperature overnight. The layers are separated and the methylene chloride layer is dried over anhydrous magnesium sulfate. The drying agent is separated by filtration and the filtrate is concentrated. The precipitated red-orange solid is collected and recrystallized from methylene chloride. The purified product weighs 7.0 g. (58% yield) and melts at 195° C.(dec.).

Analysis for: $C_{17}H_{13}NO_2S_2$. Calculated: C, 62.36; H, 4.00; N, 4.28; S, 19,59. Found: C, 62.28; H, 3.90; N, 4.23; S, 19.19.

EXAMPLE 10

3-Hydroxy-2-phenyl-5,6,7,8-tetrahydrothiazolo[2,3-b]benzothiazolium bromide 9.0 g. (0.053 moles) 2-mercapto-4,5,6,7-tetrahydrobenzothiazole and 10.75 g. (0.053 moles) α-bromophenylacetic acid are dissolved in 500 ml. of acetone, to which is further added 50 ml. each of glacial acetic acid and acetic anhydride. The mixture is heated in an open flask and the volume reduced to 100 ml. The precipitated solid is collected. The solid weighs 13 g. (67%) and melts at 233°–235° C.(dec.).

Analysis for: $C_{15}H_{14}NOS_2Br$. Calculated: C, 48.91; H, 3.83; N, 3.80; S, 17.41; Br, 21.70. Found: C, 49.10; H, 3.95; N, 3.98; S, 17.36; Br, 21.39.

EXAMPLE 11

2-Phenyl-5,6,7,8-tetrahydrothiazolo[2,3-b]-benzothiazol-3(2H)-one mesoionic dedihydro derivative 9.7 g. (0.026 moles) of 3-hydroxy-2-phenyl-5,6,7,8-tetrahydrothiazolo[2,3-b]benzothiazolium bromide, prepared according to Example 10, is suspended in a mixture of 1000 ml. methylene chloride and 500 ml. water, and the mixture is stirred at room temperature for 5 hours. The layers are separated and the methylene chloride layer is dried over anhydrous magnesium sulfate. The drying agent is removed by filtration and the filtrate is reduced in volume. The residual solid is triturated with ether and the yellow solid is collected. The crude material is recrystallized from 1.5 l. of acetonitrile to yield a yellow solid weighing 4.7 g. (63% yield). The product melts at ca. 200° C.(dec.).

Analysis for: $C_{15}H_{13}NOS_2$. Calculated: C, 62.68; H, 4.56; N, 4.87. Found: C, 62.57; H, 4.51; N, 4.83.

EXAMPLE 12

3-Acetoxy-7-chloro-2-phenylthiazolo[2',3'-2,3]-thiazolo[5,4-b]pyridinium bromide 10.1 g. (0.05 moles) 5-chloro-2-mercaptothiazolo-[5,4-b[pyridine and 10.8 g. (0.05 moles) α-bromophenylacetic acid are dissolved in 150 ml. acetone to which are added 50 ml. each of glacial acetic acid and acetic anhydride. The mixture is heated to reflux for 4 hours. The solid which precipitates is collected, and weighs 8.8 g. Heating of the filtrate yields a further 6.8 g. recovery of solid, for a total recovery of 15.6 g. (70% yield). The compound melts at 192°-195° C.

Analysis for: $C_{16}H_{10}ClN_2O_2S_2Br$. Calculated: C, 43.50; H, 2.28; N, 6.34. Found: C, 43.34; H, 2.34; N, 6.55.

EXAMPLE 13

7-Chloro-3-hydroxy-2-phenylthiazolo-[2',3'-2,3]thiazolo[5,4-b]pyridinium bromide The 3-acetoxy-7-chloro-2-phenylthiazolo[2',3'-2,3]-thiazolo[5,4-b]pyridinium bromide prepared according to Example 12 is deacetylated in hot acetone. The title compound melts at 210°-213° C.

Analysis for: $C_{14}H_{18}ClN_2OS_2Br$. Calculated: C, 42.06; H, 2.02; N, 7.01. Found: C, 41.62; H, 2.19; N, 6.80.

EXAMPLE 14

7-Chloro-2-phenylthiazolo[2',3'-2,3]-thiazolo[5,4-b]pyridin-3(2H) one mesoionic didehydro derivative The 3-acetoxy-7-chloro-2-phenylthiazolo[2',3'-2,3]-thiazolo[5,4-b]pyridinium bromide prepared according to Example 12 is suspended in a 5:1 mixture of methylene chloride and water. The layers are separated and the methylene chloride layer, after removal of most of methylene chloride, is further purified with methylene chloride. The title compound melts at 220° C. with decomposition.

Analysis for: $C_{14}H_7ClN_2OS_2$. Calculated: C, 52.74; H, 2.21; N, 8.79. Found: C, 52.77; H, 2.38; N, 8.88.

EXAMPLE 15

In cell-mediated antoimmune diseases, such as SLE, rheumatoid arthritis (RA), hemolytic anemia and so forth, there is a marked increase in the production of the IgM and IgG immunoglobulins. In the case of SLE and hemolytic anemia, the increase is systemic and appears in the serum, while in the case of rheumatoid arthritis, the increase tends to localize in the synovial fluids. The increase is itself pathologic and so treatment of the disease should be aimed at alleviating the exacerbating effects of the immunoglobulins.

In this example, the compounds of the invention are tested for their effect on antibody-secreting plaque-forming splenocytes (IgG and IgM) in the Cunningham modification of the Jerne assay. This technique is able to detect, in a quantitative manner, antibody producing cells in response to antigen stimulus in the host mouse. For study of cell-mediated immune response, sheep erythrocytes (SRBC) are used (as in the present Example), while for humoral immune response, SRBC coupled with pneumococcal polysaccharide is used.

$CDF_1$ (Balb/c × DBA/2) mice are immunized with 0.1 ml. of $10^8$ sheep erythrocytes (SRBC) intraperitonially 4-5 days before the assay. The mice are separated into groups, with one group serving as a control and all other groups receiving compounds of the invention. The treated mice are dosed with drug on day one. In order to determine IgM plaques, the mice are sacrificed on day four, and to determine IgG plaques, on day five or six. The spleens of the sacrificed mice are excised and washed several times in RPMI 1640 with 10% fetal bovine serum. 100 λ of spleen cells are mixed with a drop of guinea pig complement, four drops of RPMI 1640 and a drop of 25% SRBC in a microtiter plate well and then pipetted into a Cunningham chamber. On day four, for IgM determinations, the chambers are incubated for 30 minutes at 37° C. Antibody, released by the small proportion of active cells, attaches to the surrounding erythrocytes which are lysed by complement leaving a small plaque up to 0.5 mm. in diameter. Since only cells releasing IgM antibody form plaques directly, a "developing" serum must be added to be able to form and view IgG plaques. Thus fifth or sixth day cultured spleen cells are further treated with rabbit antimouse IgG and then incubated for 45 minutes. Both IgM and IgG plaques are counted under a stereomicroscope.

In Table 1 are given the IgM and IgG plaque counts per spleen for mice treated with 6-chloro-2-phenyl-thiazolo[2,3-b]benzothiazol-3(2H)-one mesoionic didehydro derivative and for the controls:

TABLE 1

The numbers given below are the total number of plaques per spleen.

|  | IgM plaques, mean | IgG plaques, mean |
|---|---|---|
| Day 4 | | |
| Control (½ CMC/saline) | 209,012 | 114,702 |
| Compound 100 mg/kg. | 63,993 | 37,087 |
| Day 6 | | |
| Control (½ CMC/saline) | 77,699 | 467,040 |
| Compound 100 mg/kg. | 39,679 | 152,745 |

The assay is repeated using the following compounds of the invention: 2-phenylthiazolo[2,3-b]benzothiazol-3(2H)-one mesoionic didehydro derivative (A), 6-chloro-2-(p-chlorophenyl)-thiazolo[2,3-b]benzothiazol-3(2H)-one mesoionic didehydro derivative (B) and 6-chloro-2-phenylthiazolo[2,3-b]benzothiazol-3(2H)-one mesoionic didehydro derivative (C).

TABLE 2

The numbers given below are the total number of plaques per spleen.

| Compound | Dose, mg/kg. | IgM, mean | IgG, mean |
|---|---|---|---|
| Day 4 | | | |
| Control (½ CMC/saline) | 1.0 ml. | 295,785 | 168,210 |
| A | 200 | 163,800 | 107,100 |
| B | 200 | 74,025 | 9,656 |
| C | 200 | 110,643 | 22,875 |
| Day 5 | | | |
| Control | 1.0 ml. | 142,143 | 242,570 |

TABLE 2-continued

The numbers given below are the total number of plaques per spleen.

| Compound | Dose, mg/kg. | IgM, mean | IgG, mean |
|---|---|---|---|
| (½ CMC/saline) | | | |
| A | 200 | 97,020 | 184,590 |
| B | 200 | 50,250 | 49,218 |
| C | 200 | 55,518 | 117,337 |

The results show that the compounds of the invention cause a marked reduction in the production of IgM and IgG by antibody secreting lymphocytes in response to antigen.

EXAMPLE 16

The effect of the compounds of the invention on the thymus gland is measured. $BDF_1$ mice of 18–20 gms. weight are dosed at 150 mg/kg. with 6-chloro-2-phenylthiazolo[2,3-b]benzothiazolo-3(2$\underline{H}$)-one mesoionic didehydro derivative for eight consecutive days. The mice are sacrificed on the ninth day, the thymus glands excised and weighed. The excised thymus glands averaged 21.8 gms. as compared to 55.0 gms. for the control group. Histopathological examination of the treated glands shows the weight loss to be due solely to the depletion of lymphocytes. Moreover there is some reduction in the size of the cervical, axillary, trachial and inguinal lymph nodes. The treated and excised thymus glands, after resting for three weeks, return to normal weight and histopathological status. The weight loss is also correlated to dose, and the results are as follows:

TABLE 3

| Dose, mg/kg. | Thymus weight, gms. |
|---|---|
| 200 | 20.5 |
| 150 | 21.8 |
| 100 | 11.8 |
| 50 | 46.0 |
| 12.5 | 55.3 |
| Control | 55.4 |

Using the same technique, the following compounds of the invention were tested: 6-chloro-2-(p-chlorophenyl)thiazolo[2,3-b]benzothiazol-3(2$\underline{H}$)-one mesoionic didehydro derivative (A), 2-phenyl-5,6,7,8-tetrahydrothiazolo[2,3-b]benzothiazol-3(2$\underline{H}$)-one mesoionic didehydro derivative (B), 2-phenylthiazolo[2,3-b]-benzothiazol-3(2$\underline{H}$)-one mesoionic didehydro derivative (C), 6-chloro-2-trifluoroacetylthiazolo[2,3-b]benzothiazol-3(2$\underline{H}$)-one mesoionic didehydro derivative (D), 6-chloro-3-hydroxy-2-phenylthiazolo[2,3-b]benzothiazolium bromide (E), 7-ethoxy-3-hydroxy-2-phenylthiazolo[2,3-b]benzothiazolium bromide (F), 3-hydroxy-2-phenylthiazolo[2,3-b]benzothiazolium bromide (G), and 3-hydroxy-2-phenyl-5,6,7,8-tetrahydrothiazolo[2,3-b]benzothiazolium bromide (H). The results are summarized in Table 4:

TABLE 4

| Compound | Dose, mg/kg. | Avg. weight of thymus gland, mg. | % Change in weight |
|---|---|---|---|
| Control[①] | 1.0 ml. | 39.7 | — |
| A | 200 | 18.6 | −53 |
| B | 200 | 16.8 | −58 |
| C | 200 | toxic | — |
| D | 200 | 28.4 | −28 |
| E | 75 | 17.5 | −56 |
| F | 150 | 33.3 | −16 |
| G | 75 | 28.0 | −29 |
| H | 75 | 40.5 | +2 |

[①] of 0.5% CMC + saline

All these results show that the thymus weight loss is a physiological response to the immunomodulatory agent. The thymus gland is the organ responsible for differentiating stem cells into the T cells (small lymphocytes) responsible for cell-mediated immunity. The depletion of lymphocytes in the thymus, therefore, evidences a direct and significant modulatory effect on cell-mediated immunity by the compounds of the invention.

EXAMPLE 17

The adjuvant arthritis test is performed as a secondary evaluating procedure for immunomodulatory activity.

Polyarthritis is induced in male Lewis strain rats by injection of a suspension of tubercule bacilli in mineral oil in the subplanar tissue of the right hind paw. Drug therapy is begun either on the day of antigen or after the appearance of an established arthritic syndrome. Compounds are administered daily in the form of a fine suspension by stomach tube. Body weights, left and injected right paw volumes and occurrence of arthritic nodules on the ears, tail, and front paws are determined at frequent intervals over a 14 to 21 day period. All animals are then autopsied and stress organ weights, hematology, histopathology and biochemical studies on blood proteins are done. Active compounds will either prevent or reverse the joint swelling and associated sequella of polyarthritis with minimal toxicity. The results are expressed as percent inhibition of paw edema.

The results of the test for prophylactic peroral administration of 6-chloro-2-phenylthiazolo[2,3-b]benzothiazol-3(2$\underline{H}$)-one mesoionic didehydro derivative are summarized in Table 5:

TABLE 5

| Dose, mg/kg. | Mean % Inhibition of Left Paw Edema |
|---|---|
| 10 | 32 |
| 25 | 41* |
| 50 | 63* |

*= $p < 0.05$

The results show that the compound tested shows prophylactic activity in the adjuvant arthritis model.

The results of the test for therapeutic peroral administration of 6-chloro-2-phenylthiazolo[2,3-b]benzothiazol-3(2$\underline{H}$)-one mesoionic didehydro derivative for established adjuvant arthritis are summarized in Table 6. In this test, the drug dosing begins on the sixteenth day after antigen, when adjuvant arthritis is established and continues for seven days. The paw edemas are measured on the fourth and seventh day of dosing.

TABLE 6

| Day of Measurement | Dose, mg/kg. | Mean % Inhibition of Left Paw Edema |
|---|---|---|
| 4th | 12.5 | 94* |
| 4th | 50 | 67* |
| 7th | 12.5 | 66* |

TABLE 6-continued

| Day of Measurement | Dose. mg/kg. | Mean % Inhibition of Left Paw Edema |
|---|---|---|
| 7th | 50 | 58* |

*= p < 0.05

The compound tested clearly shows therapeutic activity in the established adjuvant arthritis model.

EXAMPLE 18

The compounds of the invention are tested for regulatory activity on a delayed hypersensitivity reaction. Compounds having regulatory activity on T-lymphocytes (for example, those which increase suppressor activity and reduce lymphokine production) are active in this test.

Male Hartley strain guinea pigs are immunized with an emulsion containing equal volumes of 0.9% saline and complete adjuvant H37 Ra (Mycobacterium tuberculosis). Each animal is injected with 0.4 ml. distributed evenly among the front foot pads (i.d.) and hips (i.m.). Seven or fourteen days later each animal is challenged with 1000 units of Purified Protein Derivative (PPD) Tuberculin in saline administered intradermally in the right rear foot pad. Foot volumes are measured immediately prior to antigenic challenge and 24 and 48 hours after challenge. Drugs are administered orally on a mg/kg. basis 24 hours before or 6 hours after challenge. Test compounds are suspended or dissolved in 2.0 ml/400 kg. (body weight) of 0.5% Methocel ® methyl cellulose (100 centipoise). Controls receive only 0.5% Methocel ® methyl cellulose. The results, summarized in Table 7 for 6-chloro-2-phenylthiazolo[2,3-b]benzothiazol-3(2H)-one mesoionic didehydro derivative (A) and the commercial product cyclophosphamide (Cytoxan ®), are expressed as mean percent inhibition of paw edema at 24 hours after challenge.

TABLE 7

| Compound | Dose mg/kg. | Time of dosing | Mean % Inhibition of Paw Edema |
|---|---|---|---|
| A | 50 | 24 hours before challenge | 43* |
| Cyclophosphamide | 50 | 24 hours before challenge | 56* |
| A | 50 | 6 hours after challenge | 41* |
| Cyclophosphamide | 50 | 6 hours after challenge | 58* |

*= p < 0.05

The results show that the compound tested is at least as effective as cyclophosphamide in the guinea pig delayed hypersensitivity assay (PPD).

EXAMPLE 19

The effect of the compounds of the invention on the development and progress of autoimmune disease (systemic lupus erythematosus) in the New Zealand $F_1$ hybrid mouse (NZB×NZW) is evaluated.

NZB/W $F_1$ mice are divided into two groups according to sex. At the initiation of drug treatment, female mice are 78.2 days old with an average weight of 30 g., while male mice are 69.5 days old with an average weight of 40 g. IgG, IgM and antinuclear antibody determinations are made on pooled samples of serum obtained by capillary bleedings of the suborbital sinus at approximately monthly intervals. The compounds of the invention are suspended in a solution of physiological saline with 0.16% CMC. All dosing is twice weekly intraperitonially.

The results of immunoglobulin determinations of the autoimmune mice treated with 6-chloro-2-phenyl-thiazolo[2,3-b]benzothiazol-3(2H)-one mesoionic didehydro derivative (A) and L-(−)-2,3,5,6-tetrahydro-6-phenylimidazo[2,1-b]thiazole (levamisole) are summarized in Tables 8 and 9 for female and male NZB/W mice, respectively. Immunoglobulin values from serum samples are compared with the baseline (pretreatment) for each group.

TABLE 8

IMMUNOGLOBULIN DETERMINATIONS FEMALE [2] NZB/W MICE

| Drug | Dose mg./kg. | Immuno-globulin | Immunoglubulin Levels After Number of Days of Treatment Indicated (mg./100 ml.) | | | | | Total Change From Baseline |
|---|---|---|---|---|---|---|---|---|
| | | | Pretreatment | 47 Days | 76 Days | 111 Days | 154 Days | |
| Control[3] | 1.0 ml. | IgM | 64 | 89 | 87 | 138 | 160 | +96 |
| A | 100 | IgM | 64 | 49 | 54 | 148 | 108 | +44 |
| Levamisole | 25 | IgM | 64 | 49 | 83 | 136 | 154 | +90 |
| Control[3] | 1.0 ml. | IgG | 460 | 730 | 660 | 830 | 824 | +364 |
| A | 100 | IgG | 460 | 234 | 220 | 496 | 420 | −40 |
| Levamisole | 25 | IgG | 460 | 404 | 490 | 980 | 900 | +440 |

| | | | Highest Dilution Positive After Number of Days of Treatment Indicated | | | | | |
|---|---|---|---|---|---|---|---|---|
| Control[3] | 1.0 ml. | ANA[1] | 1:10 | 1:40 | 1:40 | 1:160 | 1:320 | |
| A | 100 | ANA[1] | 1:10 | neg. | neg. | neg. | neg. | |
| Levamisole | 25 | ANA[1] | 1:10 | 1:20 | 1:20 | 1:40 | 1:80 | |

[1] Antinuclear antibody;
[2] Virgin;
[3] of 0.5% CMC + Saline

TABLE 9

IMMUNOGLOBULIN DETERMINATIONS MALE NZB/W MICE

| Drug | Dose mg./kg. | Immuno-globulin | Immunoglobulin Levels After Number of Days of Treatment Indicated (mg./100 ml.) | | | | | Total Change From Baseline |
|---|---|---|---|---|---|---|---|---|
| | | | Pretreatment | 47 Days | 76 Days | 111 Days | 154 Days | |
| Control[2] | 1.0 ml. | IgM | 43.5 | 57 | 82 | 85 | 106 | +62.5 |
| A | 100 | IgM | 43.5 | 48 | 49 | 80 | 96 | +52.5 |

TABLE 9-continued

| IMMUNOGLOBULIN DETERMINATIONS MALE NZB/W MICE | | | | | | | | |
|---|---|---|---|---|---|---|---|---|
| Levamisole | 25 | IgM | 43.5 | 68 | 140 | 128 | 142 | +98.5 |
| Control[2] | 1.0 ml. | IgG | 450 | 630 | 550 | 820 | 790 | +390 |
| A | 100 | IgG | 450 | 234 | 240 | 240 | 324 | −126 |
| Levamisole | 25 | IgG | 450 | 560 | 710 | 710 | 910 | +460 |

| | | | Highest Dilution Positive After Number of Days of Treatment Indicated | | | | | |
|---|---|---|---|---|---|---|---|---|
| Control[2] | 1.0 ml. | ANA[1] | 1:10 | 1:10 | 1:10 | 1:10 | 1:20 | |
| A | 100 | ANA[1] | 1:10 | neg. | neg. | neg. | neg. | |
| Levamisole | 25 | ANA[1] | 1:10 | 1:20 | 1:10 | 1:10 | — | |

[1] Antinuclear antibody
[2] of 0.5% CMC + Saline

Over a period of nearly a half year, the compound of the invention which was tested successfully suppressed the development of autoimmune disease, as measured by the major criteria of IgG, IgM and antinuclear antibody suppression. The immunoglobulins are always elevated in the disease pathology of autoimmune diseases such as systemic lupus erythematosus, as well as in such disorders as rheumatoid arthritis.

Another autoimmune disease model, hemolytic anemia, is used to further evaluate the compounds of the invention. Thus, NZB mice, having an average age of 142 days and with well advanced hemolytic anemia, are divided into treatment groups and are dosed biweekly over a period of two weeks (four doses total) with the following compounds in the same manner as previously described: 6-chloro-2-(p-chlorophenyl)thiazolo[2,3-b]benzothiazol-3(2H)-one mesoionic didehydro derivative (A), 2-phenyl-5,6,7,8-tetrahydrothiazolo[2,3-b]benzothiazol-3(2H)-one mesoionic didehydro derivative (B), 2-phenylthiazolo[2,3-b]benzothiazol-3(2H)-one mesoionic didehydro derivative (C) and 6-chloro-2-trifluoroacetylthiazolo[2,3-b]benzothiazol-3(2H)-one mesoionic didehydro derivative (D). The immunoglobulin values from serum samples are compared with the baseline (pretreatment) for each group and the results are summarized in Table 10:

TABLE 10

| Drug | Dose mg./kg. | No. of Mice | Immunoglobulin | Baseline (142 Days) | 1st Reading (156 Days) | % Change |
|---|---|---|---|---|---|---|
| Control[1] | 1.0 ml. | 4 | IgG | 674 | 640 | −5% |
| A | 200 | 4 | IgG | 760 | 304 | −60% |
| B | 200 | 4 | IgG | 710 | 356 | −50% |
| C | 200 | 4 | IgG | 674 | 570 | −15% |
| D | 200 | 3 | IgG | 710 | 770 | +8% |
| Control[1] | 1.0 ml. | 4 | IgM | 188 | 220 | +17% |
| A | 200 | 4 | IgM | 176 | 120 | −32% |
| B | 200 | 4 | IgM | 194 | 134 | −31% |
| C | 200 | 4 | IgM | 146 | 176 | +21% |
| D | 200 | 3 | IgM | 182 | 190 | +4% |
| Control[1] | 1.0 ml. | 4 | ANA[2] | 1:40 | 1:160 | |
| A | 200 | 4 | ANA[2] | 1:20 | neg. | |
| B | 200 | 4 | ANA[2] | 1:20 | neg. | |
| C | 200 | 4 | ANA[2] | neg. | neg. | |
| D | 200 | 3 | ANA[2] | 1:20 | 1:20 | |

[1] of 0.5% CMC + Saline
[2] Antinuclear antibody

The results show significant reductions in pathologic immunoglobulin levels in the autoimmune hemolytic anemia in the mice by at least two of the compounds of the invention, with the other two compounds tested showing a lesser degree of activity.

EXAMPLE 20

The ability of the compounds of the invention to influence the growth and metastatic spread of murine Lewis lung carcinoma implanted subcutaneously, is evaluated.

The procedures employed for stock tumor maintenance and transfer, as well as for drug evaluation on the primary tumor, are those found in Cancer Chemotherapy Reports, Vol. 3, No. 2, September 1972, Protocol 1.400. The measurements of metastic spread are made by counting tumor foci on the excised lung under an illuminated magnifying lens or a dissecting microscope, after employment of the Wexler india ink technique (Hilda Wexler, "Accurate Identification of Experimental Pulmonary Metastases", J. Nat. Can. Inst., Volume 36, No. 4, April 1966, pp. 641–643) to accurately identify and count lung metastases.

The result of the assay are summarized as follows:

TABLE 11

| Compound | Dose, mg/kg. | Average Number of Metastases |
|---|---|---|
| 6-Chloro-2-phenylthiazolo-[2,3-b]benzothiazol-3(2H)-one mesoionic didehydro derivative | 300 | 99.1 |
| 6-Chloro-2-phenylthiazolo-[2,3-b]benzothiazol-3(2H)-one mesoionic didehydro derivative | 150 | 81.3 |
| 6-Chloro-2-phenylthiazolo-[2,3-b]benzothiazol-3(2H)-one mesoionic didehydro derivative | 100 | 38.4 |
| 6-Chloro-2-phenylthiazolo-[2,3-b]benzothiazol-3(2H)-one mesoionic didehydro derivative | 50 | 15.3 |
| 6-Chloro-2-phenylthiazolo-[2,3-b]benzothiazol-3(2H)-one mesoionic didehydro derivative | 25 | 10.8 |

TABLE 11-continued

| Compound | Dose, mg/kg | Average Number of Metastases |
|---|---|---|
| Control | — | 17.0 |

At extremely high dose levels, the results show a marked increase in numbers of metastatic lesions in treated animals as compared to the control. At the lower doses, however, there is no increase and in fact at doses at 25 and 50 mg/kg., there is even a decrease in the average number of lesions. These results correlate well with results observed with other immunomodulatory agents, but is not possible to make any conclusive observations about the possible oncological effects of the compounds of the invention.

What is claimed is:

1. A compound having the formula:

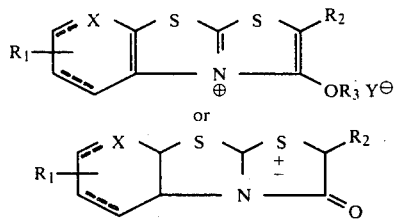

wherein $R_1$ is hydrogen, halo, amino, lower alkyl, lower alkoxy, trifluoromethyl or hydroxy;

$R_2$ is lower alkyl, acetyl, trifluoroacetyl, phenyl or phenyl substituted with fluorine, chlorine, bromine, lower alkyl, lower alkoxy, amino, nitro and trifluoromethyl;

$R_3$ is hydrogen or lower alkanoyl;

X is CH or N, with the proviso that when $R_1$ is hydrogen and X is CH, $R_2$ is not lower alkyl; and Y is $CF_3CO_2^\ominus$ or halide, and where the dotted lines represent optional double bonds in the 5,6 and 7,8 positions.

2. The compound of claim 1, having the name 6-chloro-3-hydroxy-2-phenylthiazolo[2,3-b]benzothiazolium bromide.

3. The compound of claim 1, having the name 3-hydroxy-2-phenylthiazolo[2,3-b]benzothiazolium bromide.

4. The compound of claim 1, having the name 6-chloro-2-phenylthiazolo[2,3-b]benzothiazol-3(2H)-one mesionic didehydro derivative.

5. The compound of claim 1, having the name 3-hydroxy-2-phenylthiazolo[2',3'-2,3]thiazolo[4,5-b]pyridinium trifluoroacetate.

6. The compound of claim 1, having the name 2-phenylthiazolo[2',3'-2,3]thiazolo[5,4-b]pyridin-3(2H)-one mesoionic didehydro derivative.

7. The compound of claim 1, having the name 6-chloro-2-trifluoroacetylthiazolo[2,3-b]benzothiazol-3(2H)-one mesoionic didehydro derivative.

8. The compound of claim 1, having the name 6-chloro-2-(p-chlorophenyl)thiazolo[2,3-b]benzothiazolium bromide.

9. The compound of claim 1, having the name 6-chloro-2-(p-chlorophenyl)thiazolo[2,3-b]benzothiazol-3(2H)-one mesoionic didehydro derivative.

10. The compound of claim 1, having the name 2-phenylthiazolo[2,3-b]benzothiazol-3(2H)-one mesoionic didehydro derivative.

11. The compound of claim 1, having the name 7-ethoxy-3-hydroxy-2-phenylthiazolo[2,3-b]benzothiazolium bromide.

12. The compound of claim 1, having the name 7-ethoxy-2-phenylthiazolo[2,3-b]benzothiazol-3(2H)-one mesoionic didehydro derivative.

13. The compound of claim 1, having the name 3-hydroxy-2-phenyl-5,6,7,8-tetrahydrothiazolo[2,3-b]benzothiazolium bromide.

14. The compound of claim 1, having the name 2-phenyl-5,6,7,8-tetrahydrothiazolo[2,3-b]benzothiazol-3(2H)-one mesoionic didehydro derivative.

15. The compound of claim 1, having the name 3-acetoxy-7-chloro-2-phenylthiazolo[2',3'-2,3]thiazolo[5,4-b]pyridinium bromide.

16. The compound of claim 1, having the name 7-chloro-3-hydroxy-2-phenylthiazolo[2',3'-2,3]thiazolo[5,4-b]pyridinium bromide.

17. The compound of claim 1, having the name 7-chloro-2-phenylthiazolo[2',3'-2,3]thiazolo[5,4-b]pyridin-3(2H)-one mesoionic didehydro derivative.

18. A method of modulating the immune response in warm-blooded animals in need of modulation of the immune response which comprises administering to a warm-blooded animal an amount effective to bring about said modulation of the immune response of a compound having the general formula:

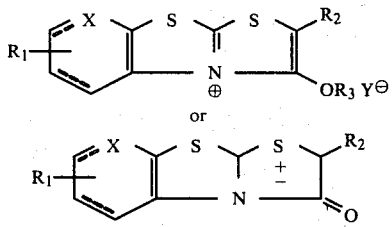

wherein $R_1$ is hydrogen, halo, amino, lower alkyl, lower alkoxy, trifluoromethyl or hydroxy;

$R^2$ is lower alkyl, acetyl, trifluoroacetyl, phenyl, or phenyl substituted with fluorine, chlorine, bromine, lower alkyl, lower alkoxy, amino, nitro, and trifluoromethyl;

$R_3$ is hydrogen or lower alkanoyl;

X is CH or N; and

Y is $CF_3CO_2^\ominus$ or a halide and where the dotted lines represent optional double bonds in the 5,6 and 7,8 positions.

* * * * *